(12) United States Patent
Harke

(10) Patent No.: US 10,599,941 B2
(45) Date of Patent: Mar. 24, 2020

(54) MULTI-FEATURE IMAGE TRACKING

(71) Applicant: Hamilton Sundstrand Corporation, Charlotte, NC (US)

(72) Inventor: Michael C. Harke, DeForest, WI (US)

(73) Assignee: HAMILTON SUNDSTRAND CORPORATION, Charlotte, NC (US)

(*) Notice: Subject to any disclaimer, the term of this patent is extended or adjusted under 35 U.S.C. 154(b) by 239 days.

(21) Appl. No.: 15/700,209

(22) Filed: Sep. 11, 2017

(65) Prior Publication Data

US 2019/0080194 A1    Mar. 14, 2019

(51) Int. Cl.
| | |
|---|---|
| G06K 9/00 | (2006.01) |
| G06K 9/32 | (2006.01) |
| G06K 9/46 | (2006.01) |
| F01D 21/00 | (2006.01) |
| G01N 21/88 | (2006.01) |
| G06T 7/00 | (2017.01) |

(52) U.S. Cl.
CPC ......... G06K 9/3216 (2013.01); F01D 21/003 (2013.01); G01N 21/8806 (2013.01); G06K 9/4604 (2013.01); G06T 7/001 (2013.01); *G01N 2021/8838* (2013.01); *G06T 2200/24* (2013.01); *G06T 2207/30164* (2013.01)

(58) Field of Classification Search
CPC ......... F01D 21/003; G01N 2021/8838; G01N 21/8806; G06K 9/3216; G06K 9/4604; G06T 2200/24; G06T 2207/30164; G06T 7/001
See application file for complete search history.

(56) References Cited

U.S. PATENT DOCUMENTS

| | | |
|---|---|---|
| 7,043,055 B1 | 5/2006 | Silver |
| 2011/0026805 A1 | 2/2011 | Hori |
| 2013/0162846 A1 | 6/2013 | Xie et al. |
| 2014/0072217 A1* | 3/2014 | Xu ................ G06K 9/3275 382/170 |
| 2015/0193923 A1* | 7/2015 | Soto .................. G06T 7/60 382/106 |
| 2017/0287147 A1* | 10/2017 | Takahashi ............ G06T 7/35 |

OTHER PUBLICATIONS

EP Application No. 18193474.6 Extended EP Search Report dated Feb. 12, 2019, 7 pages.
H Kim, et al., "Visual encoder: robust and precise measurement method of rotation angle via high-speed RGB vision," Optics Express, Jun. 8, 2016, vol. 24, No. 12, 12 pages.
W. Li, et al., "Method of rotation angle measurement in machine vision based on calibration pattern with spot array," Applied Optics, Feb. 20, 2010, vol. 49, No. 6, 6 pages.

\* cited by examiner

*Primary Examiner* — Xin Jia
(74) *Attorney, Agent, or Firm* — Cantor Colburn LLP

(57) ABSTRACT

A processing system is configured to access an image of a system under analysis including a plurality of features of interest. The processing system determines a first angular position estimate of a first feature of interest in the image and determines a second angular position estimate of a second feature of interest in the image. The processing system determines a final angular position estimate for the system under analysis based on a relationship between the first angular position estimate and the second angular position estimate. The final angular position estimate is output.

16 Claims, 7 Drawing Sheets

MULTI-FEATURE IMAGE TRACKING

BACKGROUND

The present disclosure pertains to the art of image processing, and more particularly to multi-feature image tracking for enhanced position resolution.

In some applications, a moving object must be measured without mounting a transducer to it. For instance, packaging constraints or other factors can inhibit direct measurements of position and/or motion using a position transducer. Tracking the rotary position of an electric machine with high accuracy can be challenging using traditional motion estimation techniques from a video image, as slight measurement inaccuracies can result in large deviations in measurement results.

BRIEF DESCRIPTION

According to some embodiments, a method includes accessing, by a processing system, an image of a system under analysis including a plurality of features of interest. The processing system determines a first angular position estimate of a first feature of interest in the image based on one or more edges of the first feature of interest. The processing system determines a second angular position estimate of a second feature of interest in the image based on one or more edges of the second feature of interest. The processing system determines a final angular position estimate for the system under analysis based on a relationship between the first angular position estimate and the second angular position estimate. The final angular position estimate is output.

In addition to one or more of the features described above, or as an alternative to any of the foregoing embodiments, further embodiments may include identifying a third feature of interest in the image and establishing a polarity of the final angular position estimate based on a position of the third feature of interest.

In addition to one or more of the features described above, or as an alternative to any of the foregoing embodiments, further embodiments may include where the third feature of interest comprises a region adjacent to the first feature of interest, and both the first feature of interest and the third feature of interest are located on a same component of the system under analysis.

In addition to one or more of the features described above, or as an alternative to any of the foregoing embodiments, further embodiments may include where the second feature of interest is split into two regions that are radially outward of the first feature of interest.

In addition to one or more of the features described above, or as an alternative to any of the foregoing embodiments, further embodiments may include where the first region of interest is located on a multi-colored disk, the first angular position estimate is based on an edge between at least two colors on the multi-colored disk, and the two regions of the second feature of interest are on edges of impeller blades extending from opposite sides of the multi-colored disk.

In addition to one or more of the features described above, or as an alternative to any of the foregoing embodiments, further embodiments may include limiting an angular search window to locate the second feature of interest based on the first angular position estimate of the first feature of interest.

In addition to one or more of the features described above, or as an alternative to any of the foregoing embodiments, further embodiments may include producing a first edge image based on applying a first edge detector to a first portion of the image, where the first edge image includes fewer pixels than the image, producing a second edge image based on applying a second edge detector to a second portion of the image, where the second edge image includes fewer pixels than the image, applying a transform to the first edge image to identify one or more lines projected through the first feature of interest, applying the transform to the second edge image to identify one or more lines projected through the second feature of interest, identifying an angle between at least one of the one or more lines projected through the first feature of interest relative to the at least one of the one or more lines projected through the second feature of interest having a best correlation to an expected angular offset between the first feature of interest and the second feature of interest, and using the angle to determine the final angular position estimate for the system under analysis.

In addition to one or more of the features described above, or as an alternative to any of the foregoing embodiments, further embodiments may include cropping the image to reduce image size before applying edge detection, performing a first normalization of the image to rescale pixel values in a limited range before applying edge detection, performing non-maxima suppression after applying edge detection, performing a second normalization of the image to rescale pixel values after performing non-maxima suppression.

In addition to one or more of the features described above, or as an alternative to any of the foregoing embodiments, further embodiments may include eliminating one or more portions of the image outside of a region of interest, and applying a threshold filter to remove edges below a threshold value.

In addition to one or more of the features described above, or as an alternative to any of the foregoing embodiments, further embodiments may include identifying one or more timing indicators in the image, and correlating rotational speed data of the system under analysis with the final angular position estimate based on a state of the one or more timing indicators.

According to some embodiments, a system includes a memory system operable to store a plurality of instructions and at least one processor. The at least one processor is operable to execute the instructions to access an image of a system under analysis including a plurality of features of interest, determine a first angular position estimate of a first feature of interest in the image based on one or more edges of the first feature of interest, and determine a second angular position estimate of a second feature of interest in the image based on one or more edges of the second feature of interest. The at least one processor is further operable to execute the instructions to determine a final angular position estimate for the system under analysis based on a relationship between the first angular position estimate and the second angular position estimate, and output the final angular position estimate.

Technical effects of embodiments of the present disclosure include using multiple features to track an angular position in an image with enhanced position resolution. Various image complexity reduction techniques are used to isolate the desired features of interest and reduce the risk of feature identification errors.

The foregoing features and elements may be combined in various combinations without exclusivity, unless expressly indicated otherwise. These features and elements as well as the operation thereof will become more apparent in light of the following description and the accompanying drawings.

However, it should be understood that the following description and drawings are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

A detailed description of one or more embodiments of the disclosed systems and methods are presented herein by way of exemplification and not limitation with reference to the Figures.

Embodiments can improve the accuracy of angular position estimation determined using an image. A video camera can be used to record motion of a rotating component of a machine, such as an impeller of a system under analysis. An impeller edge can be physically marked with a contrast band, such as a white band, decal, or other variation in color, reflectivity, and the like. The contrast band provides a substantial contrast variation with respect to impeller blades. However, depending on the thickness of the contrast band, multiple detectable edges can result, which can lead to detection inaccuracies if the wrong edge is tracked. Another feature that can be tracked is a central element, such as a disk, that rotates at the same rate as the impeller. Using a multi-colored disk (where black and white are considered examples of colors), another high contrast feature can be used in conjunction with the contrast band of the impeller blades to reduce positioning ambiguity and increase feature resolution. The location of colored regions on the disk can be used as a third feature to determine/confirm the polarity of the resulting position estimate, e.g., to distinguish between an angle of 30 degrees and 210 degrees for the same line.

Figure 1:
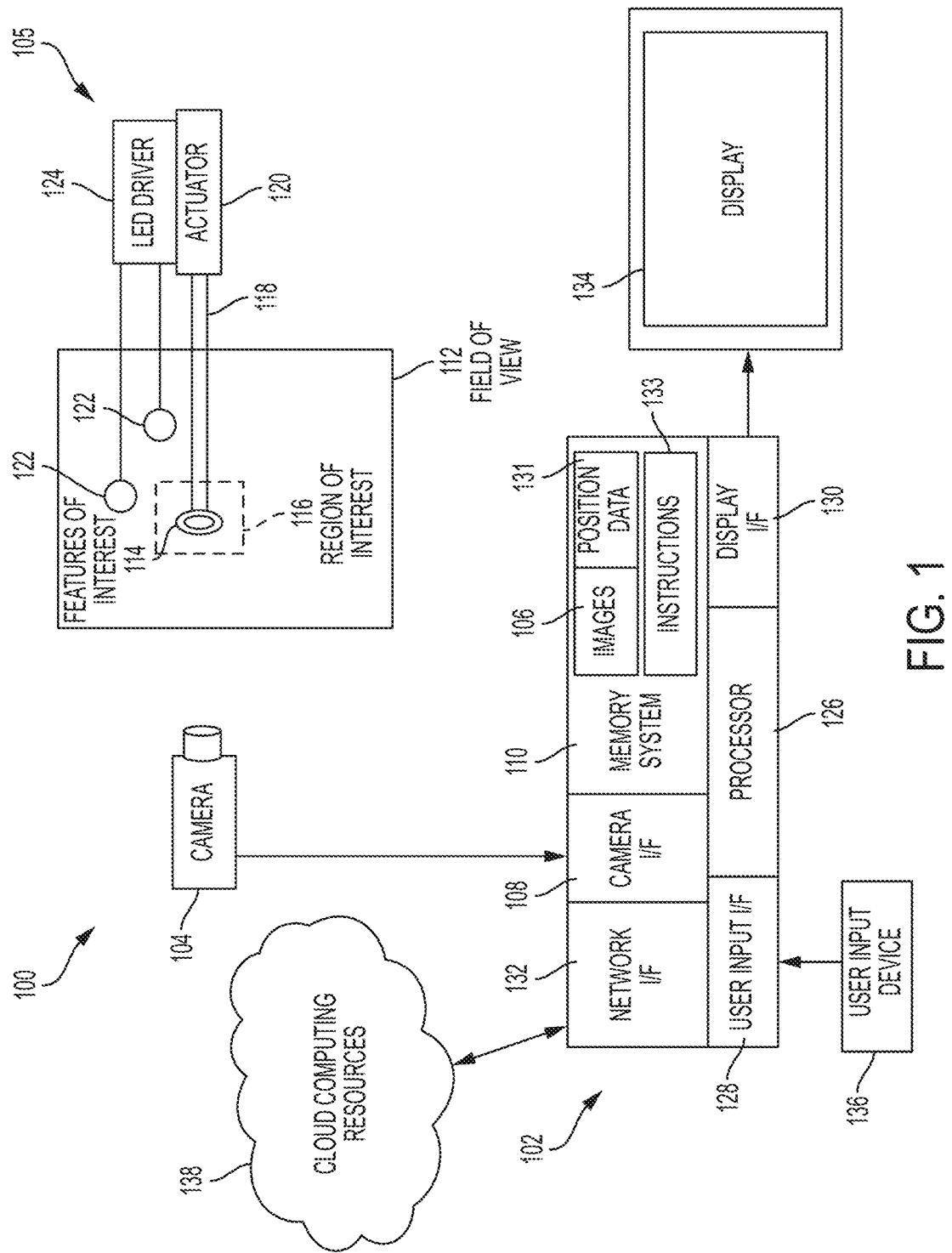
FIG. 1 illustrates a system according to an embodiment.

Referring now to FIG. 1, a system 100 is depicted that includes a processing system 102 and a system under analysis 105. The processing system 102 can receive video/image input from at least one camera 104. The camera 104 can be a high-frame rate (e.g., 8000 frames per second) camera with one or more imaging channels to capture grayscale or color video images. When an instance of the camera 104 is a color camera that produces images in a red-green-blue (RGB) color space, the color images can be merged or only a single color channel may be used to reduce the image processing burden on the processing system 102. In some embodiments, the camera 104 provides a real-time video stream of images 106 to a camera interface 108 of the processing system 102 to track features of the system under analysis 105 while in motion. Alternatively, the video stream of images 106 output by the camera 104 can be stored in a memory system 110 of the processing system 102 for later processing to confirm that operation of the system under analysis 105 was within expected performance constraints. As one example, the performance constraints can include confirming that no reverse rotation of a rotating component occurred within an accuracy tolerance.

The camera 104 can observe a field of view 112 that includes a plurality of features of interest 114 within a region of interest 116. The features of interest 114 can include one or more rotating components on a shaft 118 driven by an actuator 120 of the system under analysis 105. For example, the actuator 120 can be an electric machine that drives rotation of an impeller, and one or more of the features on interest 114 can include impeller blade edges. In the example of FIG. 1, there is no direct signal feedback from the system under analysis 105 to the processing system 102 to provide position or speed information. To assist with correlating the images 106 of motion driven by the actuator 120 with other data, one or more timing indicators 122 may be visible within the field of view 112 of the camera 104. The timing indicators 122 can be light emitting diodes (LEDs) driven by an LED driver 124 in conjunction with activation of the actuator 120. Although the timing indicators 122 can be omitted in embodiments, the timing indicators 122 may assist in correlating measured data from the system under analysis 105 with images 106 captured by the camera 104 in a light-on or light-off state. In some embodiments, one or more of the timing indicators 122 can be pulsed once per revolution of the shaft 118, pulsed at other rates, or be activated at or above a minimum speed threshold.

In embodiments, the processing system 102 can include at least one processor 126, a user input interface 128, a display interface 130, a network interface 132, and other features known in the art. The processor 126 can be any type of central processing unit (CPU), including a microprocessor, a digital signal processor (DSP), a microcontroller, an application specific integrated circuit (ASIC), a field programmable gate array (FPGA), or the like. Also, in embodiments, the memory system 110 may include random access memory (RAM), read only memory (ROM), or other electronic, optical, magnetic, or any other computer readable medium onto which is stored data, such as position data 131 and algorithms as executable instructions 133 in a non-transitory form. The position data 131 can include intermediate results of analysis of the images 106 as well as a final angular position estimate for the system under analysis 105 as further described herein. Other types of data, such as temporary image files, application programs, operating systems, and the like can also be stored in the memory system 110. The instructions 133 can be executed by the processor 126 to implement image processing and feature extraction of multiple features from the field of view 112, including the features of interest 114.

The processor 126 and/or display interface 130 can include one or more graphics processing units (GPUs) which may support vector processing using a single instruction multiple data path (SIMD) architecture to process multiple layers of data substantially in parallel for output on display 134. The user input interface 128 can acquire user input from one or more user input devices 136, such as keys, buttons, scroll wheels, touchpad, mouse input, and the like. In some embodiments the user input device 136 is integrated with the display 134, such as a touch screen. The network interface 132 can provide wireless and/or wired communication with one or more remote processing and/or data resources, such as cloud computing resources 138. The cloud computing resources 138 can perform portions of the processing described herein and may be an alternate source of the images 106 when gathered remotely.

Figure 2:
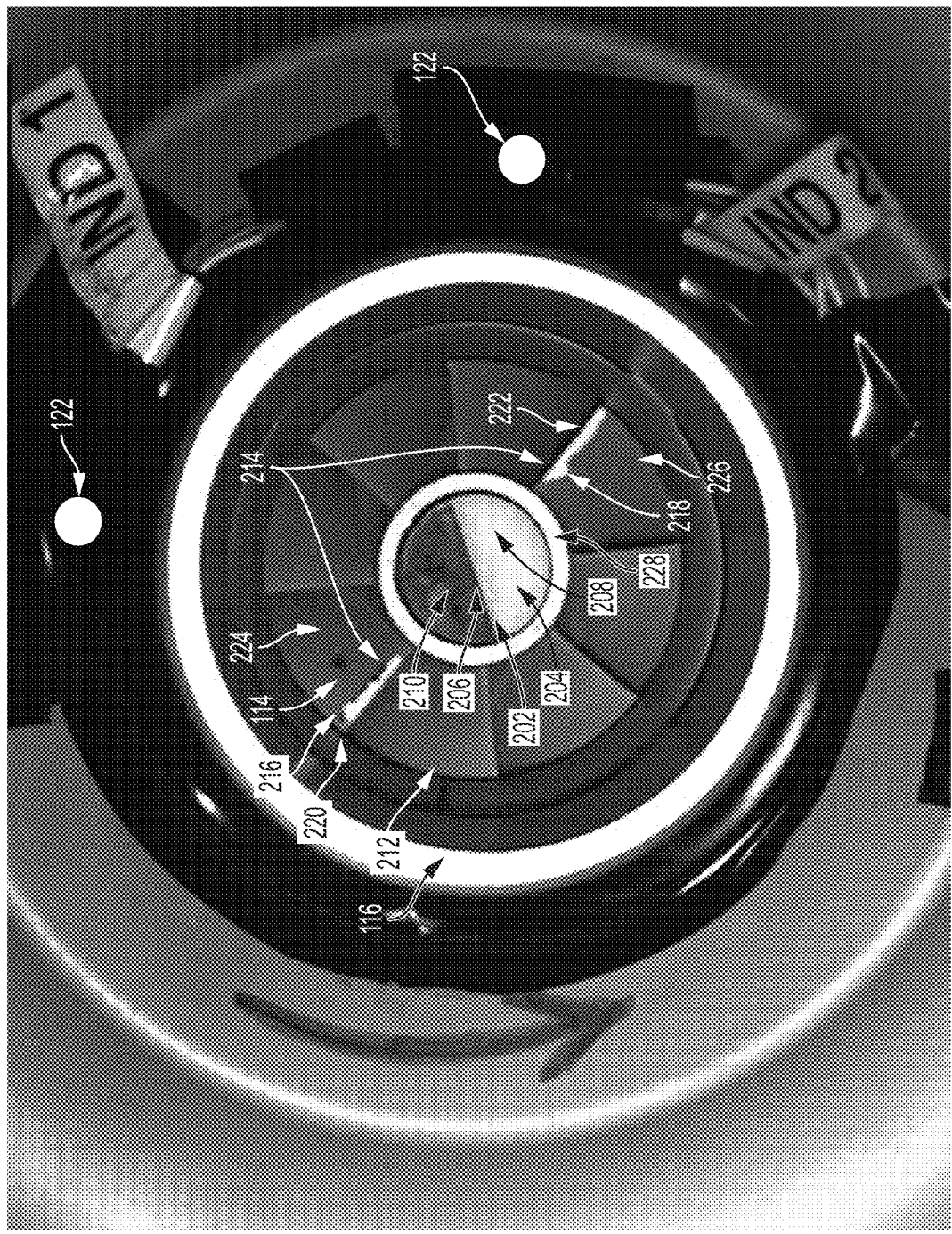
FIG. 2 illustrates an example of an image of a portion of a system under analysis according to an embodiment.

FIG. 2 depicts an example of an image 200 of a portion of the system under analysis 105 of FIG. 1 according to an embodiment. The image 200 is an example of the types of images 106 that can be captured by the camera 104 of FIG. 1. Image data captured in the image 200 represents the field of view 112 of FIG. 1, which can include features of interest 114 in the region of interest 116. The features of interest 114 can include, for example, a contrast line 202 on a multi-colored disk 204 as a first feature of interest 206, where the contrast line 202 is a border between a lighter section 208 and a darker section 210 of the multi-colored disk 204. The multi-colored disk 204 can be black and white or any other combination of colors that provides a substantial contrast in the image 200. The multi-colored disk 204 can be driven to rotate by the shaft 118 of FIG. 1 in combination with impeller 212. A second feature of interest 214 can be formed between a first contrast band 216 and a second contrast band 218 that highlight edges 220, 222 respectively of a first impeller blade 224 and a second impeller blade 226 on opposite sides of the multi-colored disk 204. The first and second contrast bands 216, 218 can have varying widths and need not be uniform. A transition region 228 can provide a contrast gap between the multi-colored disk 204 and the impeller 212 to assist in isolating features of the multi-colored disk 204 from features of the impeller 212.

Figure 3:
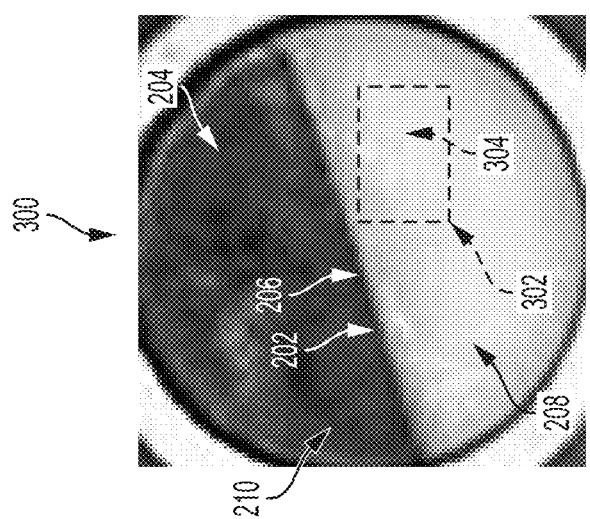
FIG. 3 illustrates a portion of FIG. 2 in greater detail according to an embodiment.
Figure 6:
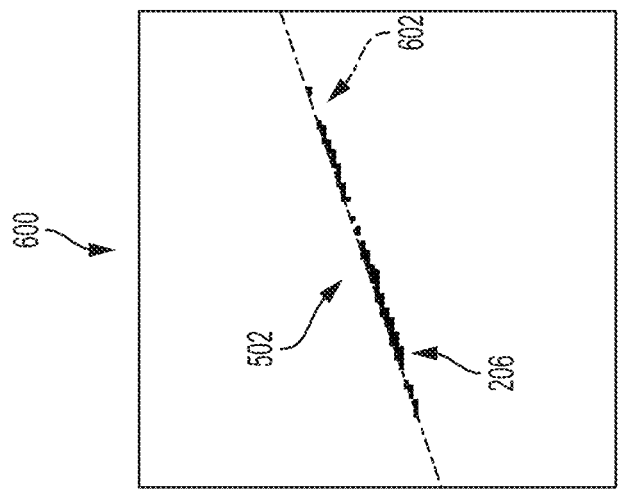
FIG. 6 illustrates an example of a line projected through a feature of interest according to an embodiment.
Figure 5:
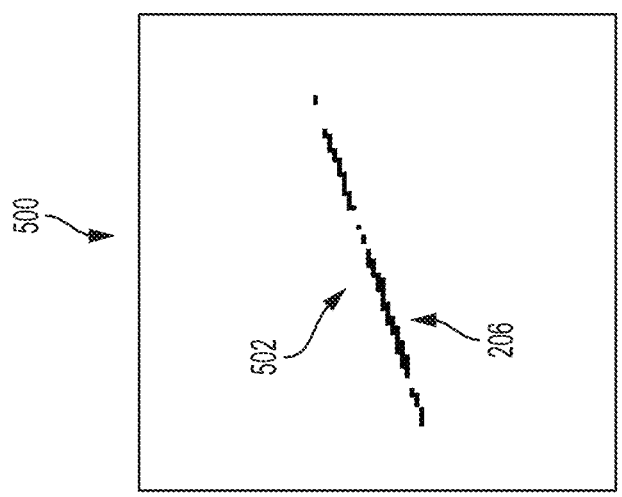
FIG. 5 illustrates an example of an edge image after reduction according to an embodiment.
Figure 8:
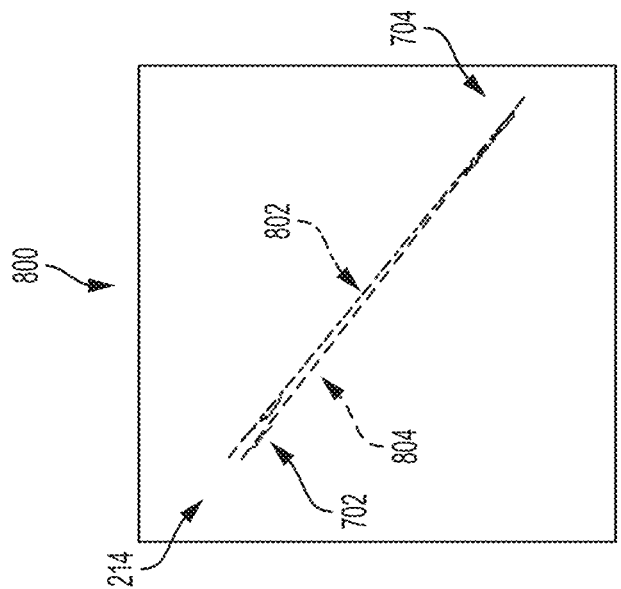
FIG. 8 illustrates an example of multiple lines projected through a feature of interest according to an embodiment.
Figure 7:
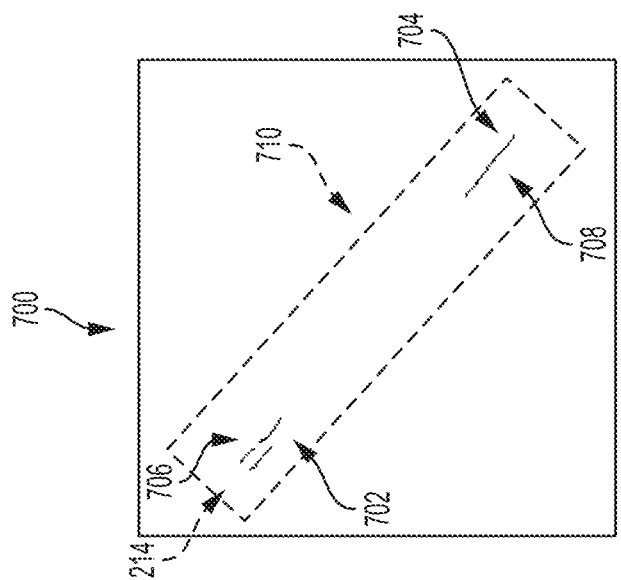
FIG. 7 illustrates an example of an edge image after reduction according to an embodiment.

FIG. 3 depicts the multi-colored disk 204 of FIG. 2 in greater detail in sub-image 300. In order to accurately determine an angle of the contrast line 202 that forms a border between the lighter section 208 and the darker section 210 of the multi-colored disk 204, the relative location of the lighter section 208 and the darker section 210 can be confirmed by analyzing a region 302. The region 302 can be selected as an area adjacent to the contrast line 202 to ensure that pixels of the region 302 are within the multi-colored disk 204 and not another component. Intensity values of pixels in the region 302 can be summed or averaged to determine whether the region 302 more closely aligns with an expected intensity of the lighter section 208 or the darker section 210. The region 302 provides a third feature of interest 304 to confirm the orientation of the contrast line 202 as the first feature of interest 206. For instance, if the lighter section 208 is above the darker section 210, then the polarity of a first angular position estimate of the first feature of interest 206 would be 180 degrees different than if the lighter section 208 is below the darker section 210. This polarity information can also impact searches for the second feature of interest 214 of FIG. 2, as well as establishing the polarity of a final angular position estimate of the edges 220, 222 of impeller blades 224, 226 and/or the contrast line 202.

Figure 4:
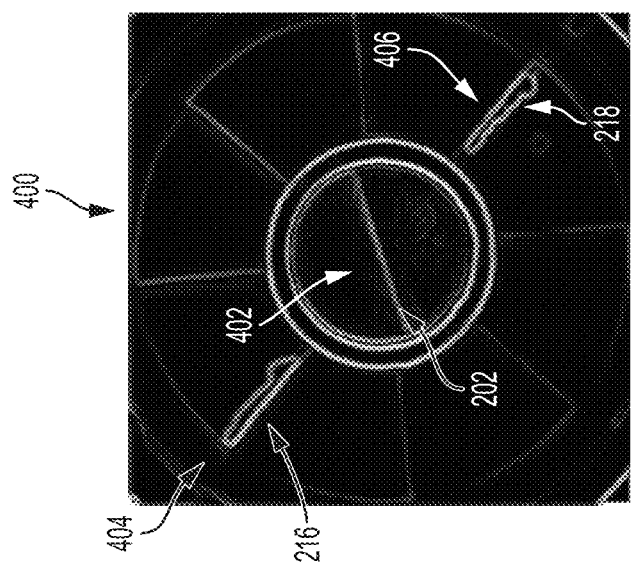
FIG. 4 illustrates an example of an image after initial processing according to an embodiment.

FIG. 4 depicts an example of edge detection processing results 400 of applying to an edge detector to a portion of the image 200 of FIG. 2. Image noise in the edge detection processing results 400 can be cleaned up by applying various pre and post processing techniques. For example, the processing system 102 can perform cropping of the image 200 to reduce the image size before applying edge detection. The processing system 102 can also perform a first normalization of the image 200 to rescale pixel values in a limited range before applying edge detection. The normalization can rescale pixel values from a range of 0-255 to a range of 0-1. The edge detection algorithm itself can be a known edge detection algorithm, such as a Canny or Deriche edge detector, to find intensity gradients in the image 200. In embodiments where a feature of interest is sufficiently narrow (e.g., about 2 pixels thick), the use of an edge detection algorithm that finds higher gradients can be omitted. As can be seen in FIG. 4, a number of edges are highlighted in the edge detection processing results 400, including an edge 402 of the contrast line 202, multiple edges 404 of the first contrast band 216, and multiple edges 406 of the second contrast band 218. To accurately identify features and positions of features in the edge detection processing results 400, further processing is performed as described in reference to FIGS. 5-10.

Figure 9:
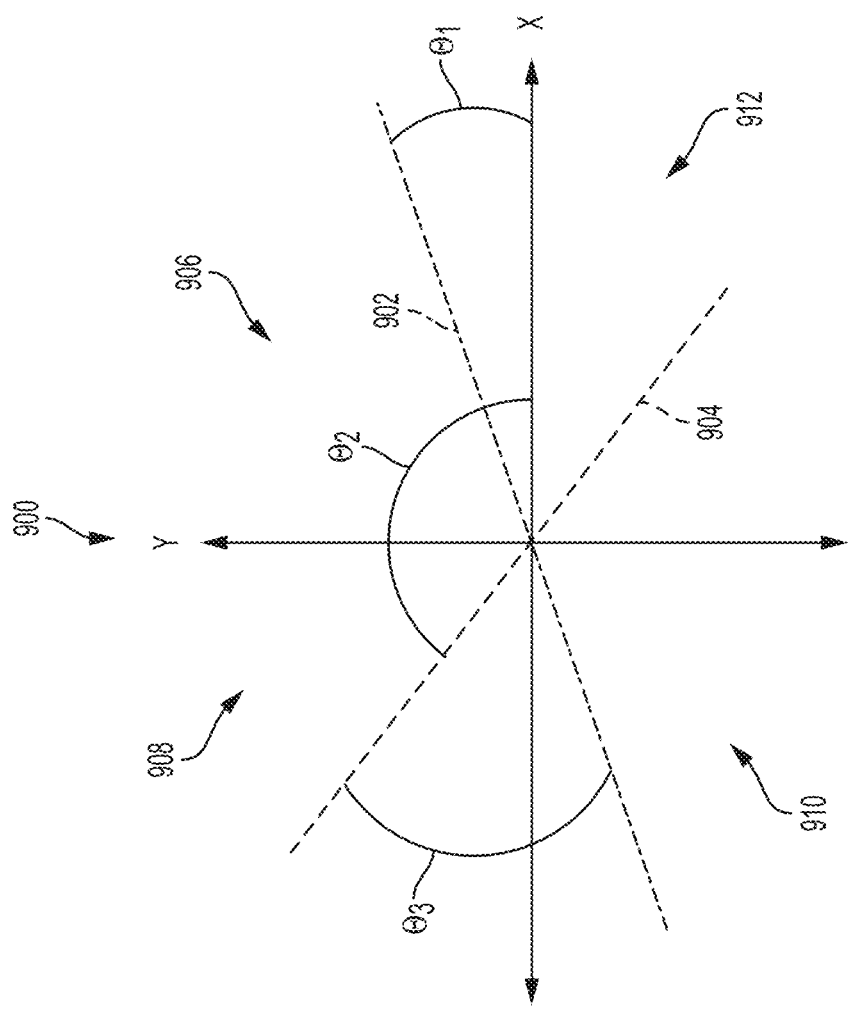
FIG. 9 illustrates an example of relationships between multiple features according to an embodiment.
Figure 10:
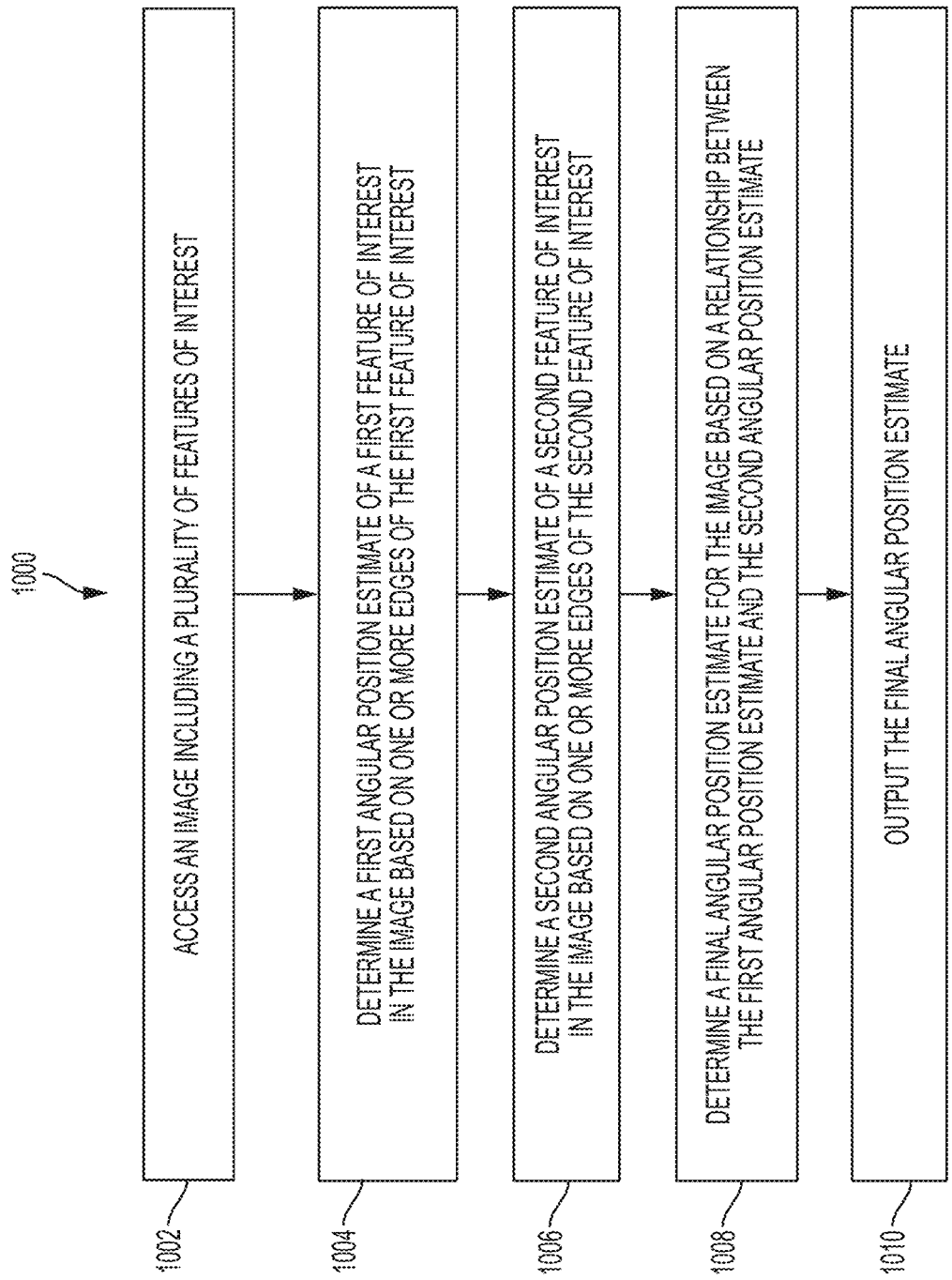
FIG. 10 illustrates a process according to an embodiment.

FIGS. 5-8 depict various views of images that can be produced using a method 1000 of FIG. 10 for position determination using multi-feature image tracking based on the image 200 of FIG. 2 in accordance with an embodiment, and FIG. 9 illustrates an example of angular relationships of features according to an embodiment. The method 1000 of FIG. 10 is described in reference to FIGS. 1-10 and may be performed with an alternate order and include additional steps. The method 1000 can be performed by the processing system 102 of FIG. 1 by executing instructions 133 stored in the memory system 110.

At block 1002, the processing system 102 accesses an image 200 of the system under analysis 105 including a plurality of features of interest 114 from images 106. The processing system 102 can perform several preprocessing steps to reduce the number of computations and complexity of subsequent image processing steps, such as cropping and applying a first normalization of the image 200 to rescale pixel values in a limited range before applying edge detection as previously described with respect to FIG. 4. Cropping can reduce the analysis area for edge detection processing from a larger field of view 112 to a region of interest 116 by trimming away an outer frame of the image 200, such as the size reduction from FIG. 2 to FIG. 4.

At block 1004, the processing system 102 determines a first angular position estimate of a first feature of interest 206 in the image 200 based on one or more edges of the first feature of interest 206. The first edge detector can use a known edge detection algorithm, such as a Canny or Deriche edge detector, to find intensity gradients in the image 200. If sufficient contrast, line length, and position resolution can be achieved by directly analyzing the image 200, the use of a more processing-intensive edge detector algorithm can be omitted. The first feature of interest 206 can be located on the multi-colored disk 204. The first angular position estimate can be based on an edge 402 between at least two colors on the multi-colored disk 204, such as the lighter section 208 and the darker section 210 of the multi-colored disk 204. Applying the first edge detector and further post-processing, including cropping, can produce an image 500 of a sparse edge 502 that represents a filtered version of the edge 402. Due to gaps in the sparse edge 502 and variations in thickness of the sparse edge 502, one or more lines 602 may be projected through the sparse edge 502. A transform, such as a Hough transform, can be applied to find a best fit instance of lines 602 through the sparse edge 502.

At block 1006, the processing system 102 determines a second angular position estimate of a second feature of interest 214 in the image 200 based on one or more edges of the second feature of interest. The second edge detector can use a known edge detection algorithm, such as a Canny or Deriche edge detector, to find intensity gradients in the image 200. As previously described, if sufficient contrast, line length, and position resolution can be achieved by directly analyzing the image 200, the use of a more processing-intensive edge detector algorithm can be omitted. Applying the second edge detector and further post-processing, including cropping, can produce an image 700 of sparse edges 702, 704 that represent a filtered version of the multiple edges 404, 406. The second feature of interest 214 can be split into two regions 706, 708 that are radially outward of the first feature of interest 206. The two regions 706, 708 of the second feature of interest 214 can be on edges 220, 222 of first and second impeller blades 224, 226 extending from opposite sides of the multi-colored disk 204. An angular search window 710 to locate the second feature of interest 214 can be limited based on the first angular position estimate of the first feature of interest 206. For example, the position, orientation, and angle of the first feature of interest 206 can be used in combination with known physical relationships between the contrast line 202 and the edges 220, 222 to limit the angular search window 710 in image 700 and find the sparse edges 702, 704 corresponding to regions 706, 708.

To reduce image noise further, several post-processing steps can be used after line detection. For example, non-maxima suppression can be performed after applying edge detection for both the first and second edge detectors. Non-maxima suppression is an edge thinning technique to reduce blurring by suppressing gradient values to zero except where a local maxima occurs which indicates a sharpest change in intensity values. A second normalization can be performed to rescale pixel values after performing non-maxima suppression. The second normalization can rescale a post-line detection image 500, 700, for instance, to values from 0-1 prior to performing a subsequent transform to produce lines 602 in image 600 and lines 802, 804 in image 800. Further processing may also include eliminating one or more portions of the image 500, 700 outside of a region of interest 116, for instance, by blacking out areas of the image 500, 700, and applying a threshold filter to remove edges below a threshold value. When physical features of an image are known, blacking out regions that are not of interest can be performed by determining expected locations of features that may vary within an expected radius range and locations greater than and/or less than the expected radius range can be blacked out (e.g., set pixel values to zero). The threshold filtering can also remove pixels from consideration that are within the expected radius range but have a gradient value lower than a minimum threshold value, e.g., less than 25%.

In some embodiments a transform, such as a Hough transform, is used to determine a line that is a best fit through pixels identified through edge detection. Line fitting may result in multiple lines 802, 804 due to separation in sparse edges 702, 702. Various potential error sources can be reduced in embodiments to lower position measurement errors due to incorrect edge identification and/or misalignment of camera 104. As an example, a first edge image, such as image 500, can be produced based on applying the first edge detector to a first portion of the image 200, where the first edge image has fewer pixels than the image 200. A second edge image, such as image 700, can be produced based on applying the second edge detector to a second portion of the image 200, where the second edge image has fewer pixels than the image 200. A transform can be applied to the first edge image to identify one or more lines 602 projected through the first feature of interest 206, as depicted in image 600. The transform can be applied to the second edge image to identify one or more lines 802, 804 projected through the second feature of interest 214, as depicted in image 800. An angle can be identified between at least one of the one or more lines 602 projected through the first feature of interest 206 relative to the at least one of the one or more lines 802, 804 projected through the second feature of interest 214 having a best correlation to an expected angular offset between the first feature of interest 206 and the second feature of interest 214. The expected angular offset can be known based on pre-existing alignment information or learned through observation of multiple images 106. Correlation results between the first feature of interest 206 and the second feature of interest 214 can be combined using a weighting factor to give preference to data associated with either the first or second feature of interest 206, 214.

At block 1008, the processing system 102 determines a final angular position estimate for the system under analysis 105 based on a relationship between the first angular position estimate and the second angular position estimate. For example, the angle resulting from correlating the transform results for the first and second features of interest 206, 214 can be used to determine the final angular position estimate for the system under analysis 105. The final angular position estimate can be mapped to the first feature of interest 206 or the second feature of interest 214, e.g., tracking the edge 402 of the multi-colored disk 204 or the edges 220, 222 of impeller blades 224, 226. An example of these relationships is depicted in plot 900, where line 902 is the best fit and correlation version of lines 602, and line 904 is the best fit and correlation between lines 802, 804. The first angular position estimate ($\Theta_1$) is defined as an angular offset of line 902 with respect to an X-axis. The second angular position estimate ($\Theta_2$) is defined as an angular offset of line 904 with respect to the X-axis. An expected angular offset ($\Theta_3$) is defined between lines 902, 904. In this example, the second angular position estimate ($\Theta_2$) can be located and confirmed based on the first angular position estimate ($\Theta_1$) and the expected angular offset ($\Theta_3$), where the final angular position estimate is equivalent to the second angular position estimate ($\Theta_2$) after confirming that the polarity is correct (e.g., not off by 180 degrees). As previously noted, the processing system 102 can also identify a third feature of interest 304 in the image 200. A polarity of the final angular position estimate can be established based on a position of the third feature of interest 304. The third feature of interest 304 can include a region 302 adjacent to the first feature of interest 206, and both the first feature of interest 206 and the third feature of interest 304 can be located on a same component of the system under analysis 105, such as the multi-colored disk 204. For instance, confirming the polarity can be used to verify that the line 904 should be located in the second and fourth quadrants 908, 912 of the plot 900 rather than in the first and third quadrants 906, 910 of the plot 900.

At block 1010, the final angular position estimate is output. Output can be logged in the position data 131 stored in the memory system 110 and/or to the display 134. The position data 131 can be linked with the images 106 in a region of the memory system 110 and may also be tagged with synchronization data based on the detected state of the timing indicators 122 captured from the image 200. The synchronization can enable accurate correlation of the position data 131 with data captured at the system under analysis 105 or observed through other test and diagnostic systems (not depicted). For instance, the processing system 102 can identify one or more timing indicators 122 in the image 200 and correlate rotational speed data of the system under analysis 105 with the final angular position estimate based on a state (light-on/light-off) of the one or more timing indicators 122.

The various functions described above may be implemented or supported by a computer program that is formed from computer readable program codes and that is embodied in a computer readable medium. Computer readable program codes may include source codes, object codes, executable codes, and others. Computer readable mediums may be any type of media capable of being accessed by a computer, and may include Read Only Memory (ROM), Random Access Memory (RAM), a hard disk drive, a compact disc (CD), a digital video disc (DVD), or other forms.

Terms used herein such as component, module, system, and the like are intended to refer to a computer-related entity, either hardware, a combination of hardware and software, or software execution. By way of example, a component may be, but is not limited to, a process running on a processor, a processor, an object, an executable, a thread of execution, a program, and/or a computer. It is understood that an application running on a server and the server may be a component. One or more components may reside within a process and/or thread of execution and a component may be localized on one computer and/or distributed between two or more computers.

The term "about" is intended to include the degree of error associated with measurement of the particular quantity based upon the equipment available at the time of filing the application. For example, "about" can include a range of ±8% or 5%, or 2% of a given value.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure is described with reference to exemplary embodiments, it will be understood by those skilled in the art that various changes may be made and equivalents may be substituted without departing from the spirit and scope of the present disclosure. In addition, various modifications may be applied to adapt the teachings of the present disclosure to particular situations, applications, and/or materials, without departing from the essential scope thereof. The present disclosure is thus not limited to the particular examples disclosed herein, but includes all embodiments falling within the scope of the appended claims.

What is claimed is:

1. A method comprising:
    accessing, by a processing system, an image of a system under analysis including a plurality of features of interest;
    determining, by the processing system, a first angular position estimate of a first feature of interest in the image based on one or more edges of the first feature of interest, wherein the first region of interest is located on a multi-colored disk, and the first angular position estimate is based on an edge between at least two colors on the multi-colored disk;
    determining, by the processing system, a second angular position estimate of a second feature of interest in the image based on one or more edges of the second feature of interest wherein the second feature of interest is split into two regions that are radially outward of the first feature of interest, and the two regions of the second feature of interest are on edges of impeller blades extending from opposite sides of the multi-colored disk;
    determining, by the processing system, a final angular position estimate for the system under analysis based on a relationship between the first angular position estimate and the second angular position estimate; and
    outputting the final angular position estimate.

2. The method of claim 1, further comprising:
    identifying a third feature of interest in the image; and
    establishing a polarity of the final angular position estimate based on a position of the third feature of interest.

3. The method of claim 2, wherein the third feature of interest comprises a region adjacent to the first feature of interest, and both the first feature of interest and the third feature of interest are located on a same component of the system under analysis.

4. The method of claim 1, further comprising:
    limiting an angular search window to locate the second feature of interest based on the first angular position estimate of the first feature of interest.

5. The method of claim 1, further comprising:
    identifying one or more timing indicators in the image; and
    correlating rotational speed data of the system under analysis with the final angular position estimate based on a state of the one or more timing indicators.

6. A method comprising:
    accessing, by a processing system, an image of a system under analysis including a plurality of features of interest;
    determining, by the processing system, a first angular position estimate of a first feature of interest in the image based on one or more edges of the first feature of interest;
    determining, by the processing system, a second angular position estimate of a second feature of interest in the image based on one or more edges of the second feature of interest;
    determining, by the processing system, a final angular position estimate for the system under analysis based on a relationship between the first angular position estimate and the second angular position estimate, wherein determining the final angular position estimate further comprises:
        producing a first edge image based on applying a first edge detector to a first portion of the image, wherein the first edge image comprises fewer pixels than the image;
        producing a second edge image based on applying a second edge detector to a second portion of the image, wherein the second edge image comprises fewer pixels than the image;
        applying a transform to the first edge image to identify one or more lines projected through the first feature of interest;

applying the transform to the second edge image to identify one or more lines projected through the second feature of interest;

identifying an angle between at least one of the one or more lines projected through the first feature of interest relative to the at least one of the one or more lines projected through the second feature of interest having a best correlation to an expected angular offset between the first feature of interest and the second feature of interest; and using the angle to determine the final angular position estimate for the system under analysis; and outputting the final angular position estimate.

7. The method of claim 6, further comprising:
cropping the image to reduce image size before applying edge detection;
performing a first normalization of the image to rescale pixel values in a limited range before applying edge detection;
performing non-maxima suppression after applying edge detection; and
performing a second normalization of the image to rescale pixel values after performing non-maxima suppression.

8. The method of claim 7, further comprising:
eliminating one or more portions of the image outside of a region of interest; and
applying a threshold filter to remove edges below a threshold value.

9. A system comprising:
a memory system operable to store a plurality of instructions; and
at least one processor configured to execute the instructions to:
access an image of a system under analysis including a plurality of features of interest;
determine a first angular position estimate of a first feature of interest in the image based on one or more edges of the first feature of interest, wherein the first region of interest is located on a multi-colored disk, and the first angular position estimate is based on an edge between at least two colors on the multi-colored disk;
determine a second angular position estimate of a second feature of interest in the image based on one or more edges of the second feature of interest, wherein the second feature of interest is split into two regions that are radially outward of the first feature of interest, and the two regions of the second feature of interest are on edges of impeller blades extending from opposite sides of the multi-colored disk;
determine a final angular position estimate for the system under analysis based on a relationship between the first angular position estimate and the second angular position estimate; and
output the final angular position estimate.

10. The system of claim 9, wherein the at least one processor is configured to execute the instructions to:
identify a third feature of interest in the image; and
establish a polarity of the final angular position estimate based on a position of the third feature of interest.

11. The system of claim 10, wherein the third feature of interest comprises a region adjacent to the first feature of interest, and both the first feature of interest and the third feature of interest are located on a same component of the system under analysis.

12. The system of claim 9, wherein the at least one processor is configured to execute the instructions to:
limit an angular search window to locate the second feature of interest based on the first angular position estimate of the first feature of interest.

13. The system of claim 9, wherein the at least one processor is configured to execute the instructions to:
identify one or more timing indicators in the image; and
correlate rotational speed data of the system under analysis with the final angular position estimate based on a state of the one or more timing indicators.

14. A system comprising:
a memory system operable to store a plurality of instructions; and
at least one processor configured to execute the instructions to:
access an image of a system under analysis including a plurality of features of interest;
determine a first angular position estimate of a first feature of interest in the image based on one or more edges of the first feature of interest;
determine a second angular position estimate of a second feature of interest in the image based on one or more edges of the second feature of interest;
determine a final angular position estimate for the system under analysis based on a relationship between the first angular position estimate and the second angular position estimate, wherein the final angular position estimate is further determined by execution of the instructions to:
produce a first edge image based on applying a first edge detector to a first portion of the image, wherein the first edge image comprises fewer pixels than the image;
produce a second edge image based on applying a second edge detector to a second portion of the image, wherein the second edge image comprises fewer pixels than the image;
apply a transform to the first edge image to identify one or more lines projected through the first feature of interest;
apply the transform to the second edge image to identify one or more lines projected through the second feature of interest;
identify an angle between at least one of the one or more lines projected through the first feature of interest relative to the at least one of the one or more lines projected through the second feature of interest having a best correlation to an expected angular offset between the first feature of interest and the second feature of interest; and
use the angle to determine the final angular position estimate for the system under analysis; and
output the final angular position estimate.

15. The system of claim 14, wherein the at least one processor is configured to execute the instructions to:
crop the image to reduce image size before applying edge detection;
perform a first normalization of the image to scale pixel values in a limited range before applying edge detection;
perform non-maxima suppression after applying edge detection; and
perform a second normalization of the image to scale pixel values after performing non-maxima suppression.

16. The system of claim 15, wherein the at least one processor is configured to execute the instructions to:

eliminate one or more portions of the image outside of a region of interest; and apply a threshold filter to remove edges below a threshold value.

* * * * *